(12) United States Patent
Razdolsky et al.

(10) Patent No.: US 6,171,313 B1
(45) Date of Patent: Jan. 9, 2001

(54) DISTRACTION APPARATUS FOR SUBAPICAL OSTEOTOMY AND VERTICAL SEGMENT DISTRACTION AND RIDGE AUGMENTATION

(76) Inventors: Yan Razdolsky, 600 Lake Cook Rd., Suite 150, Buffalo Grove, IL (US) 60089; Patrick John Driscoll, 203 E. Olive, Prospect Heights, IL (US) 60070

(*) Notice: Under 35 U.S.C. 154(b), the term of this patent shall be extended for 0 days.

(21) Appl. No.: 09/407,944

(22) Filed: Sep. 29, 1999

Related U.S. Application Data

(63) Continuation-in-part of application No. 09/109,380, filed on Jul. 2, 1998.

(51) Int. Cl.[7] .................................................... A61F 5/00
(52) U.S. Cl. ................................. 606/86; 433/7; 606/71
(58) Field of Search .................. 606/86, 69, 70, 606/71, 105, 60; 433/2, 7, 18, 24, 173

(56) References Cited

U.S. PATENT DOCUMENTS

| 5,810,812 | * | 2/1999 | Chin | 606/53 |
| 5,873,715 | * | 2/1999 | Liou | 433/18 |

* cited by examiner

Primary Examiner—John J. Wilson
Assistant Examiner—Melba Bumgarner
(74) Attorney, Agent, or Firm—Wenderoth, Lind & Ponack, L.L.P.

(57) ABSTRACT

An apparatus for use in dental base regeneration has a support bar having fixing members on ends thereof for fixing the bar to teeth of the mandible or maxilla. A bone section engagement member, such as a fork or spade, is connected to a shaft and is inserted into a bone section resulting from osteotomy. A mechanism connects the support member with the shaft for vertical translation of the shaft. Thus, the bone section can be gradually vertically distracted to allow tissue to regenerate and gradually augment the bone ridge of the maxilla or the mandible.

19 Claims, 11 Drawing Sheets

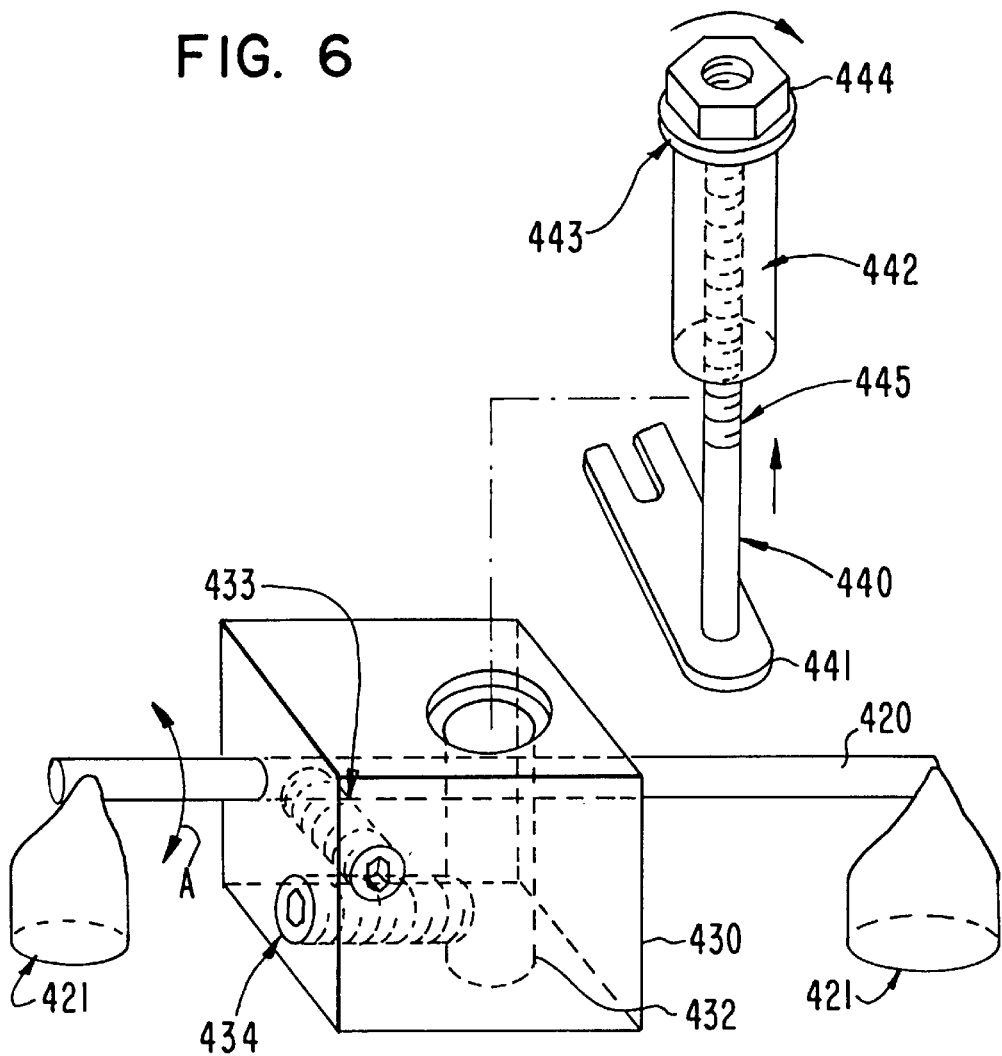

DISTRACTION APPARATUS FOR SUBAPICAL OSTEOTOMY AND VERTICAL SEGMENT DISTRACTION AND RIDGE AUGMENTATION

This application is a Continuation-in-Part of application Ser. No. 09/109,380 filed Jul. 2, 1998.

BACKGROUND OF THE INVENTION

1. Field of the Invention

The present invention relates to the field of oral surgery in general, and more specifically to the area of ridge augmentation of the maxilla and mandible.

2. State of the Prior Art

There are many known appliances in the prior art, used in various ways for different procedures in orthodontics. Of particular interest is applicants' mandibular distraction device as disclosed in U.S. Pat. No. 5,622,493. This device can be attached to the teeth of the mandible or maxilla for purposes of distraction after performing corticotomy. However, this device is not suitable for ridge augmentation.

Another device employed in distraction is disclosed in U.S. Pat. No. 5,364,396, employing a plurality of bone-attached screw devices. U.S. Pat. No. 4,713,000 to Rosenberg, and U.S. Pat. No. 4,571,178, also to Rosenberg, both disclose molar controlling and positioning dental appliances. However, none of these devices are suitable for ridge augmentation.

SUMMARY OF THE INVENTION

Applicants have recognized that where tooth loss may have occurred in the mandible or maxilla or where periodontal breakdown (disease) has occurred, bone deterioration can begin. That is, horizontal bone loss can occur, causing a dip or concavity along the line of the maxilla or mandible. For various reasons it is desirable to regenerate this bone. Accordingly, applicants have recognized that by performing a subapical osteotomy, and then vertically distracting the segment of bone generated in the subapical osteotomy, the bone ridge of the maxilla or mandible can be augmented, and bone tissue be restored. The method involves the gradual distraction of the bone section that has been cut in a vertical direction, i.e. in the direction in which bone regeneration is desired. The gradual distraction allows new tissue to develop at the point of distraction, so that the bone section is essentially "lifted" into place with new tissue developing around and underneath it. Thus it can be seen that the process is gradual, and it should be performed at a rate on the order of about 1 millimeter per day.

In order to perform the procedure, a suitable apparatus is necessary. Thus, applicants have developed the apparatus according to the present invention, which includes a support member that is adapted to be fixed with respect to one of the mandible and the maxilla, a bone section engagement member that is adapted to engage a bone section of one of the mandible and the maxilla, and a movement mechanism that connects the bone section engagement member with the support member for movement of the bone section engagement member relative to the support member.

Preferably, the support member comprises fixing members connected thereto for fixing the support member relative to one of the mandible and the maxilla. The fixing members can be bonded to the teeth or attached by caps, bands, removable attachments as with the attachments disclosed in applicants U.S. Pat. No. 5,735,688, which is hereby incorporated by reference. Bone plates can also be used to attach the fixing members, but bonding to the teeth is preferable.

The support member preferably comprises a bar that has the fixing members thereon for fixing the bar. The bone section engagement member includes a shaft that extends at an angle relative to the bar, and preferably substantially perpendicularly, and the movement mechanism includes a rotatable actuator and an engagement mechanism that engages the rotatable actuator with a shaft.

The movement mechanism includes a pivot block that is pivotally mounted on the bar and houses the rotatable actuator and the engagement mechanism. The engagement mechanism includes helical gear portions on the rotatable actuator and on the shaft of the bone section engagement member. Fine thread portions are provided on the shaft, and an internally threaded helical collar is provided which receives the shaft therein, engaging the fine thread portions, and has the helical gear portion of the shaft on the exterior thereof.

The rotatable actuator may also comprise a rotatable nut, with the engagement mechanism comprising internal threads of the nut and external threads of the shaft. In this variation, an unthreaded bearing can be provided in the pivot block to support the shaft at a position spaced from the rotatable nut.

The rotatable actuator can also comprise a rotatable thrust device that has a thrust collar for engagement with the pivot block. The engagement mechanism in this variation includes internal threads in the rotatable thrust device and external threads on the shaft. The thrust device preferably has a head and an upper surface of the pivot block for external rotation. The head may be a nut, or can be similar to a screw or bolt head. The pivot bar preferably comprises a through hole having a thrust shoulder at an upper end thereof for receiving the thrust device, with the thrust collar engaging the thrust shoulder.

The pivot block itself preferably comprises two through holes that are angled with respect to each other, one of the through holes receiving the bar, and the other receiving the shaft. Set screws are provided for locking both the bar and the shaft in position.

The bone section engagement member preferably comprises a fork that is connected to the shaft, the fork being adapted to engage the bone section. The fork can be made of a malleable material so as to be bendable, so that it can be adjusted in position, and further preferably forms a slight acute angle with the shaft. The fork can also be made of a stiff material.

In alternate embodiments, a rotatable distracting member is mounted between two fixing members, and orthodontic wire is used to attach to the bone segment for distraction thereof The end of the wire is connected with the member, so that upon rotation of the member, distraction of the segment takes place.

With the apparatus as described above, the present invention forms an apparatus that can be used in dental base regeneration, and includes an engagement means used for engaging a bone section of one of the mandible and the maxilla for distraction of the bone section after subapical osteotomy has been performed to form the bone section at a location in which the dental base regeneration is desired. With the apparatus as described above, there is further formed a distracting means connected between the support member and the engagement means for vertically distracting the bone section to permit dental based regeneration by vertically moving the engagement means relative to the support member in a precise and uniform manner over a period of time.

BRIEF DESCRIPTION OF THE DRAWINGS

Further objects, features and advantages of the present invention will become clear from the following description of preferred embodiments of the invention when taken together with the accompanying drawing figures, in which:

FIG. 6 is a partially exploded perspective view of a fourth preferred embodiment of a distraction device according to the present invention;

DETAILED DESCRIPTION OF THE PREFERRED EMBODIMENTS

Figure 1:
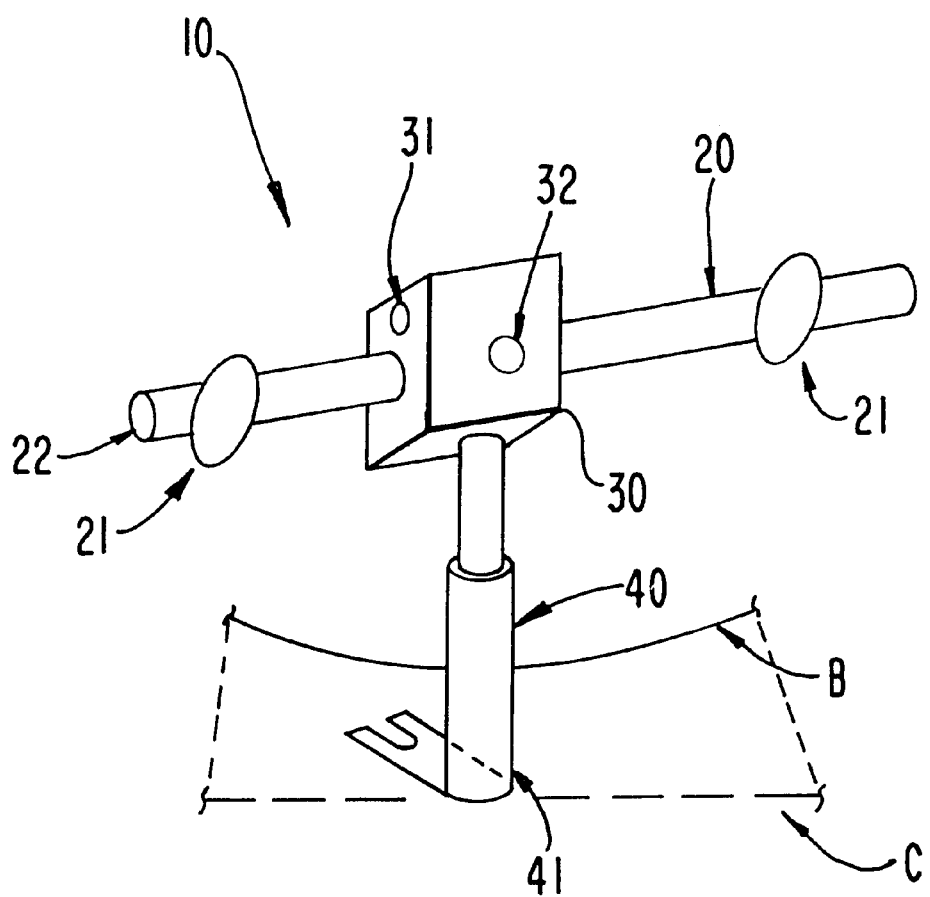
FIG. 1 is a schematic and conceptual illustration of the present invention.

Turning first to FIG. 1, attention should first be directed to the lines illustrating a bone section of the mandible Reference B illustrates the ridge of the mandible, and the dashed lines designated C, illustrate where the corticotomy is performed. Thus, a bone section is cut vertically and horizontally about a point where the bone of the mandible (or maxilla) is concave, i.e., has undergone horizontal bone loss. It is this section of the bone that is intended to be distracted.

A distraction device 10 is schematically illustrated in FIG. 1. Generally speaking, the distraction device 10 includes a bar 20 to be supported on the mandible or the maxilla. The length of the bar can be adjusted or sized to the appropriate and necessary size. Reference numbers 21 represent bonding points at which points the bar can be bonded to suitable members or attached via removable attachments for attachment to teeth, for example, to support the bar. Such members can include caps, bands, etc. Such member could also include a bone plate and/or removable attachments as described in U.S. Pat. No. 5,735,688. The diameter of the end 22 of the bar can be sized appropriately to fit into an eyelet of a bone plate for supporting the ends of the bar in position on the mandible. Thus, with the bar 20 supported at either end on the mandible, the bar is fixed at two points at opposite sides from a point at which distraction will take place.

Reference number 30 represents a pivot block that is pivoted on the bar 20. The block is simply an intermediate member interconnecting the parts of the distraction device that will connect the bone section with the supporting bar 20. A through hole is formed in the pivot block so that it can pivot on the bar 20, the bar 20 thus preferably being round. Pivoting the block is appropriate so that the block can be pivoted to move the bone engagement components into position. A set screw 32 is provided for securing the pivoted position of the pivot block on the bar 20. (It is of course noted that the bar 20 should be fixed on the mandible or maxilla so that the bar 20 itself cannot rotate about its axis.)

An arm 40, whose length can be adjustable, is provided for supporting a fork 41. The fork 41 is used to engage the bone section, and the arm (or shaft) 40 extends through a through hole on the pivot block 30. A mechanism, such as a screw 31, is used to vertically move the shaft 40. Thus gradual adjustment of the screw 31 results in gradual vertical displacement of the fork 41, and thus the bone section.

The bar 20, by being fixed to, preferably, the teeth of the mandible or maxilla, extends horizontally, horizontally in this case meaning along the line of the teeth of the mandible or the maxilla. Defining this direction as horizontal, the vertical direction is thus defined as perpendicular or substantially perpendicular to this horizontal direction. That is, the teeth are substantially perpendicular to this direction. Distraction will thus take place in this vertical direction. In this application, the term "substantially perpendicular" relative to the support bar 20 is meant to indicate the direction which may be perpendicular, but will also allow such variation as can happen depending on the alignment and direction of the teeth and the amount of variation that can be permitted and may be desired in certain circumstances, considering the direction of distraction and the osteotomy. This same meaning applies to the term "substantially vertical", vertical not being used in its strict sense, but with respect to the "horizontal" line of the teeth along the mandible or the maxilla.

Figure 2:
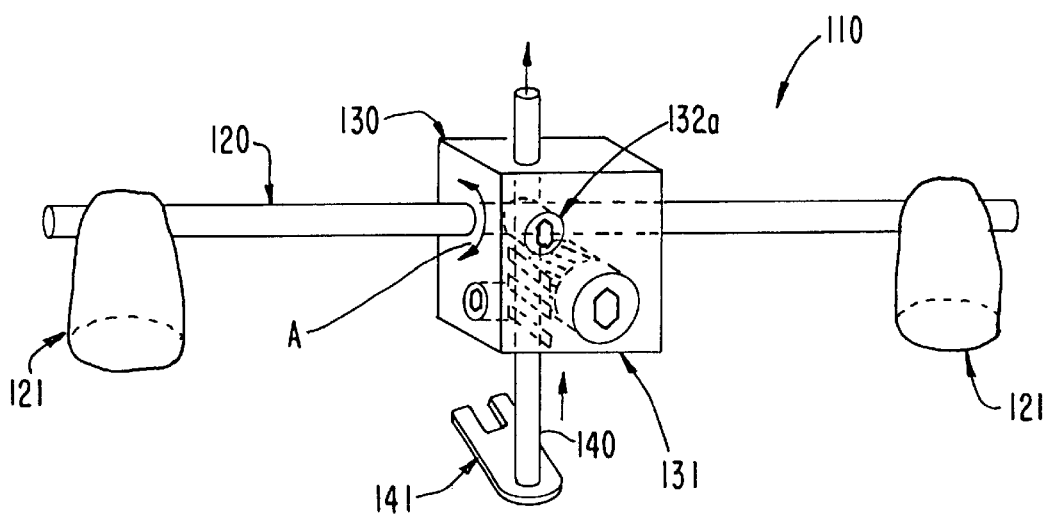
FIG. 2 is a perspective view of a first preferred embodiment of a distraction device according to the present invention.

A specific, first, preferred embodiment of the present invention is illustrated in FIG. 2. This embodiment is generally designated 110, and includes a support bar 120. Illustrated with the support bar 120 are stainless steel bands or caps 121 used to attach the support bar to the teeth. For example, the tooth on either side of a site of the osteotomy is used as a location site for the support shaft 120. A pivot block 130 is pivotally mounted on the support bar 120, the support bar 120 extending through a through hole and the pivot block 130 being pivotable about the support bar 120 as indicated by arrow A. A locking set screw 132A is used to lock the pivoted position of the pivot block 130. The fork or spade 141 is shown at the bottom of shaft 140. The fork or spade 141, by the pivoting of the pivot block 130, can pivot into position into the osteotomy site to engage the bone section. The spade 141 should not rotate about the axis of the shaft 140, but should only be permitted to vertically translate.

For purposes of vertically translating the shaft 140, there are provided crossed helical gear shafts. That is, helical gears are provided on the shaft 140 and on a rotatable actuator 131 as illustrated. By fly rotation of the rotatable actuator 131, the helical gears thereon engage with the helical gears of the shaft 140 for vertical translation of the shaft 140, as indicated by the arrows adjacent to the shaft 140. The rotatable actuator 131 is mounted in the pivot block 130 so that it can rotate about its axis. It can be actuated, for example, by means of an allen wrench, screw driver, or other suitable actuating device.

Figure 3:
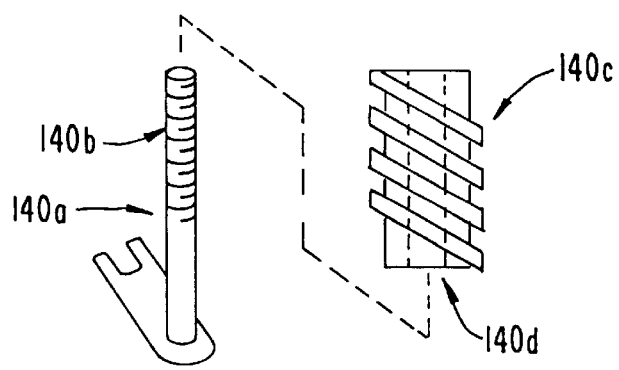
FIG. 3 is an exploded perspective view of a variation of part of the first embodiment of FIG. 2.

Suitable means may be provided for preventing the pivoting of the shaft 140 about its axis, to prevent the pivoting or rotation of the spade 141. One way of preventing rotation at the osteotomy site is illustrated in FIG. 3. Illustrated here, the shaft 140A has normal fine pitch threads formed thereon. A helical collar 140C is provided with internal threads adapted to engage with the normal fine pitch threads 140B, the internal threads of the helical collar 140C being designated by 140D. The helical gear of the shaft 140 is thus provided on the exterior of the helical collar 140C, as illustrated.

Figure 4:
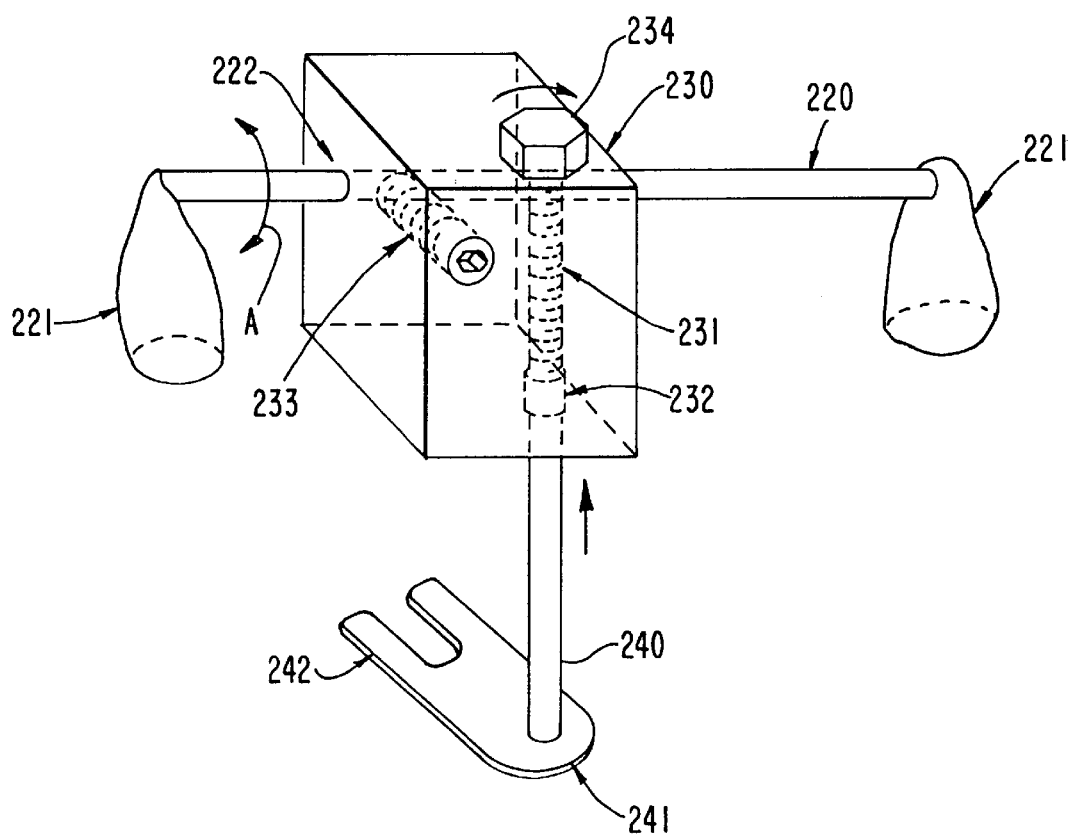
FIG. 4 is a perspective view of a distraction device according to a second preferred embodiment according to the present invention.

Turning now to FIG. 4, another embodiment of the present invention is illustrated in perspective view. In this embodiment, a support bar 220 is rotatably received in a through hole 222 of a pivot block 230, as indicated by arrow A, but with a snug fit. The pivot block 230, which is preferably made of stainless steel, is further provided with an anti-pivot locking set screw 233 for engaging the support bar 220. Stainless steel caps are indicated by reference numbers 221 at the ends of the support bar 220.

Reference 241 indicates the spade or fork according to this embodiment, which is similar to the other embodiments. It should be noted that the spade can be made of stainless steel, but may have malleable feet at the end, designated by reference number 242, for being able to form on the spade 241. The spade 241 is preferably brazed or silver soldered to the shaft 240.

The mechanism for vertically moving the shaft 240, and thus the spade 241, relative to the support bar 220 in this embodiment primarily involves the use of a nut 234 (illustrated as a hexagonal nut). The nut 234 is engaged with threads 231 on the spade shaft 240. Rotation of the nut thus results in the vertical translation of the spade shaft 240. Preferably the nut and threads are so designed so that two turns of the nut results in 1 millimeter of vertical distraction. However, this is only an example, and variations are possible in the distraction of the bone section.

Reference number 232 refers to a non-threaded bearing area that has the same diameter as the major diameter of the threads 231. This portion is formed on the shaft 240 for purposes of providing a bearing in the through hole receiving the shaft 240 of the pivot block 230.

It is noted that in this embodiment there is no set screw employed for the spade shaft 240. This assumes that the distracted segment or bone section places tension vertically downward. If necessary, however, an additional locking set screw for the spade shaft 240, or possibly a locking nut on the bottom of the pivot block 230, can be provided. One disadvantage of this arrangement, however, is that the shaft 240 has its threaded end necessarily extending all the way up to the nut 234 at the top of the pivot block 230. Thus, as distraction proceeds, the shaft 240 will extend out the top of the pivot block 230. It will thus be necessary for the orthodontist to trim off the protruding shaft after each distraction.

Figure 5:
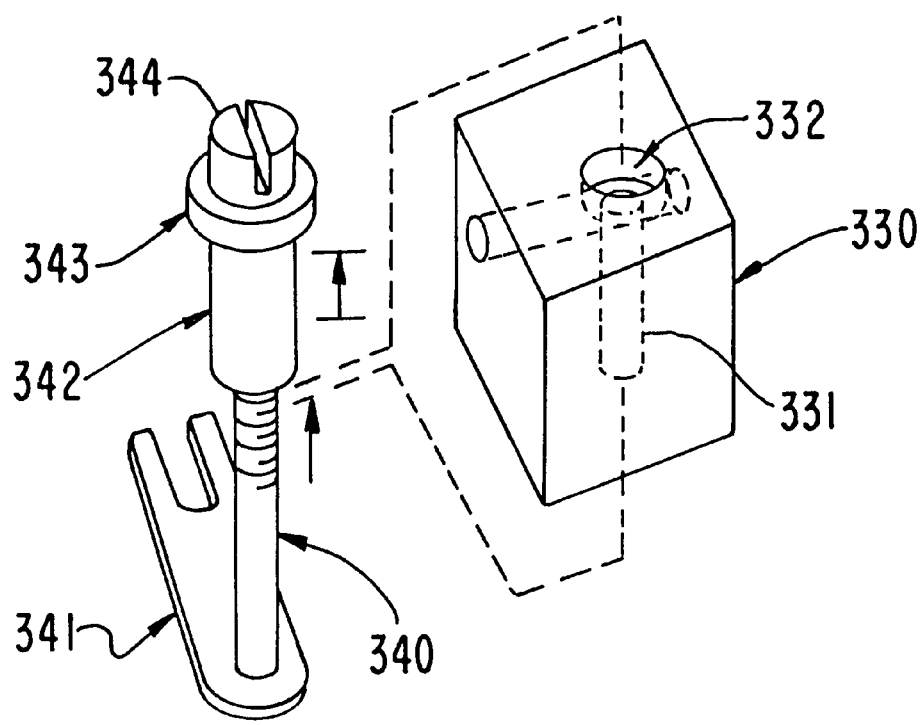
FIG. 5 is a partially exploded view of a third preferred embodiment of a distraction device according to the present invention.

A somewhat different arrangement is illustrated in FIG. 5. This arrangement employs a pivot shaft similar to the other embodiments, and thus illustration of the specifics of the pivot shaft is omitted for purposes of demonstrating this embodiment.

In this embodiment, a pivot block 330 is provided with a through hole 331 and a thrust shoulder 332. On the spade shaft 340, there is provided a thrusting device 342 that includes a thrust collar 343 and a head 344. Thus, the thrust collar 343 engages with the thrust shoulder 332, and upon rotation of the head 344, vertical translation of the shaft 340 is caused.

A variation of this embodiment is demonstrated in FIG. 6. In this embodiment, a support bar 420 has caps 421 thereon and is pivotally connected with the pivot block 430 through a through hole in the pivot block 430. Rotation of the pivot block 430 about the bar 420 can thus take place, as indicated by arrow A. A locking set screw is indicated by reference number 433 for the pivot bar 420.

A through hole 432 is provided vertically in the pivot block 430 for receiving a hollow thrust member 442 having internal threads for engaging external threads 445 of a spade shaft 440 having a spade 441 mounted at a lower end thereof. A thrust collar 443 is provided at the upper end of the thrust device 442, and has a nut/head 444. A thrust shoulder similar to that illustrated in FIG. 5 is provided at the upper end of the through hole of the pivot block 430. The thrust collar 443 thus engages the thrust shoulder, and upon rotation of the nut/head 444, the shaft 440 is caused to vertically translate inside the thrust device 442.

An advantage of this arrangement is that by extending the thrust device 442 to the majority of the extent of the through hole in the pivot block 430, the amount of vertical movement that can be permitted is increased. Furthermore, there can be a great deal of vertical movement without having the shaft 440 protrude from the top of the nut/head 444, thus necessitating less trimming of the shaft upon distraction by the orthodontist.

A thrust device lock down set screw 434 is provided, communicating with through hole 432 for the purpose of locking the thrust device 442 in position so that the shaft 440 is not translated when translation is not desired.

Figure 6A:
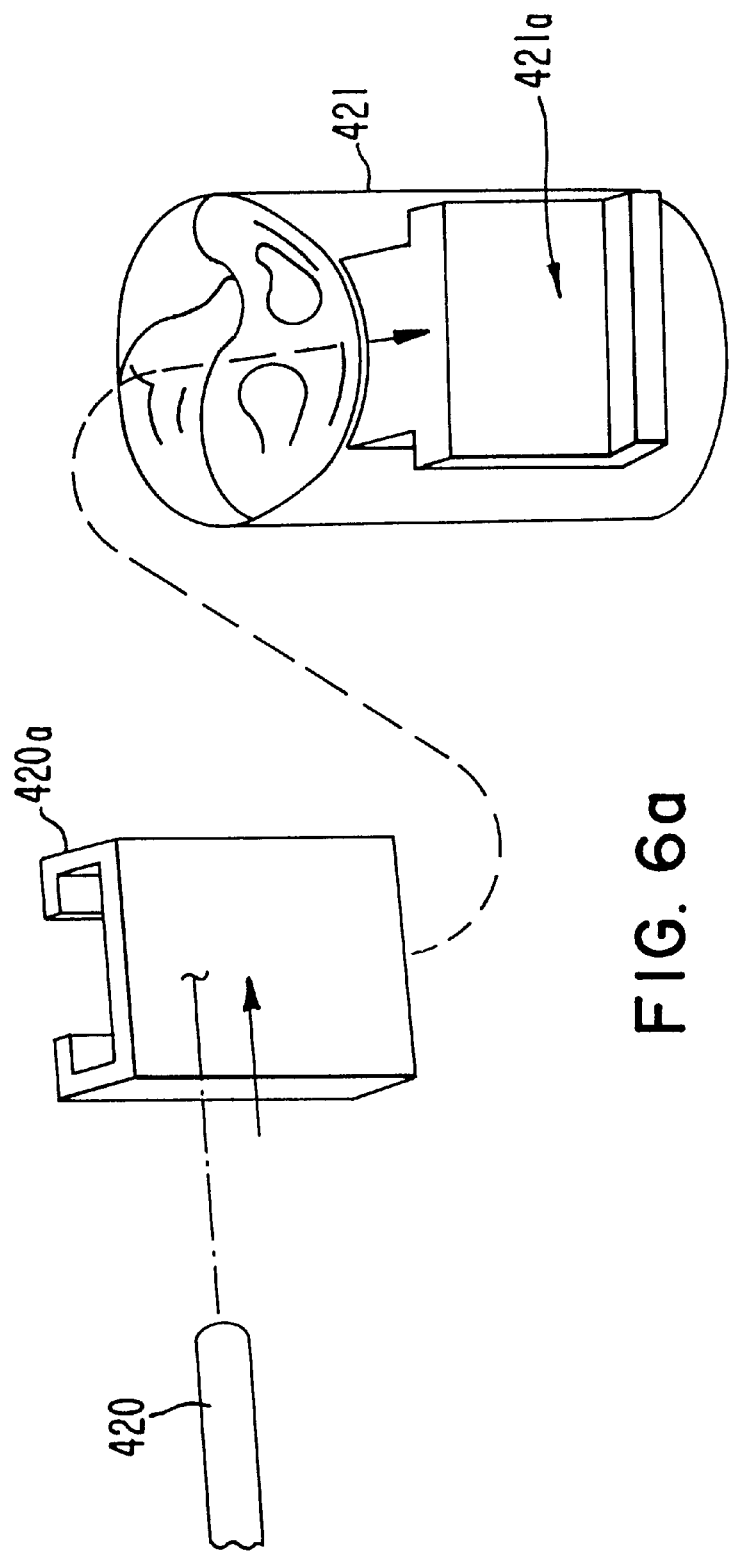
FIG. 6a is a partial perspective view of one way of connecting a bar to fixed members or teeth.

FIG. 6a is an illustration of the use of removable attachments in accordance with U.S. Pat. No. 5,735,688 with the support bar 420 and cap 421 of the embodiment of FIG. 6. As can be seen from FIG. 6a, the support bar 420 can be soldered or otherwise suitably attached to a connector attachment 420a. The connector attachment 420a can be suitably slid on to, from above, a support attachment 421a. The support attachment 421a can be appropriately soldered or otherwise attached to the cap 421. Otherwise, it might be contemplated that the cap 421 be dispensed with altogether, and the support attachment 421a directly bonded to the tooth.

The use of the attachments in accordance with U.S. Pat. No. 5,735,688 allows for the distraction device to be quickly and easily attached to the teeth after the attachments are in place on their respective support bar and on the teeth. It will of course be recognized that other suitable attachments than the one illustrated in FIG. 6a, such as the remaining ones disclosed in U.S. Pat. No. 5,735,688, for example, can be employed with a support bar 420 (or those of the other embodiments) of the present invention.

Figure 7:
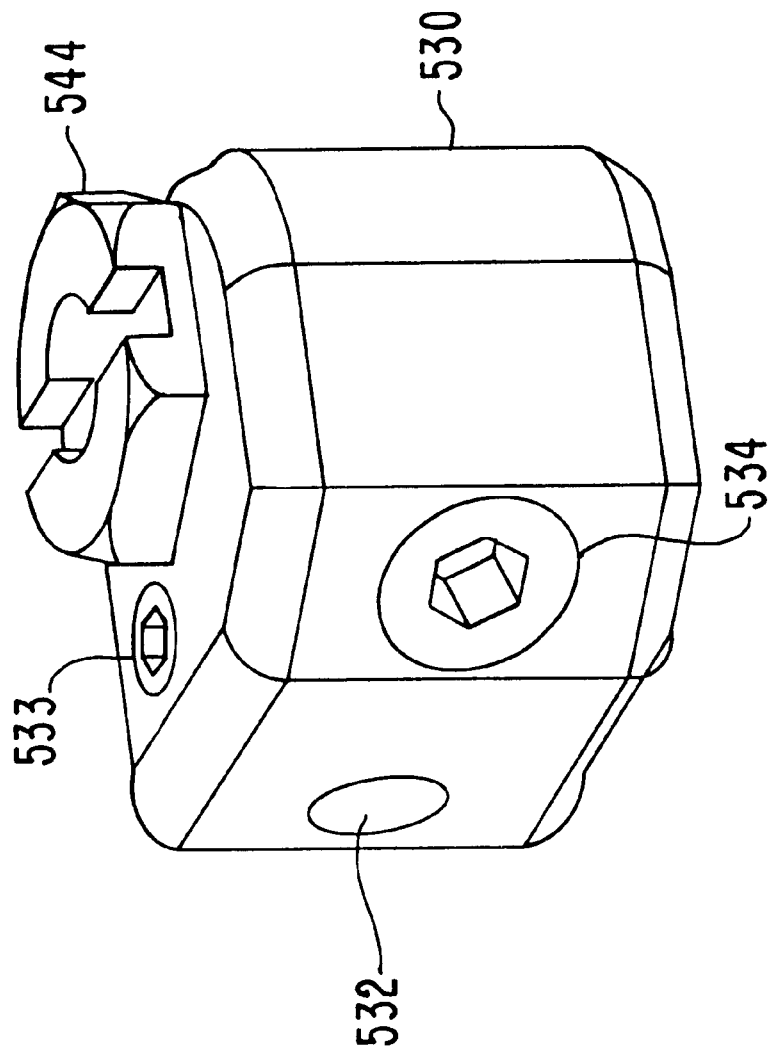
FIG. 7 is a perspective view of a preferred embodiment of a pivot block of a distraction device according to the present invention.

FIG. 7 illustrates a preferred embodiment of a pivot block 530 according to the present invention. The pivot block 530 includes a through hole 532 for a support bar, a set screw 533 for locking the support bar in place, and a thrust device lock down set screw 534. A nut/head 544 is illustrated, which can be an activating nut/head for activation of a thrust device similar to that of the embodiment of FIG. 6, for example.

Thus, it can be seen that while the basic components are similar to the remaining embodiments of the present invention, the embodiment of FIG. 7 provides an advantageous arrangement of the pivot block allowing it to be used in any position, either on the right or left side, or with the upper or lower teeth, and still retain accessibility for the locking set screw for the thrust collar in order for the orthodontist to proceed with gradual bone distraction.

Figure 7C:
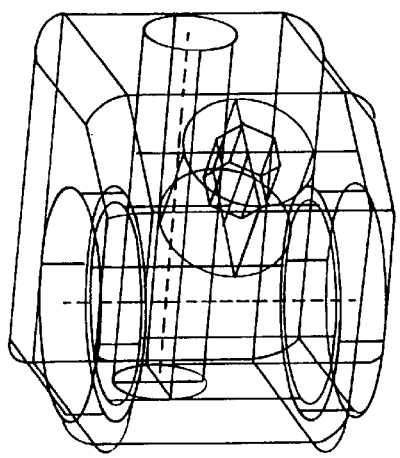
FIGS. 7a–7c are perspective views of the pivot block of FIG. 7 showing the block as if it were transparent so as to illustrate internal features of the pivot block.
Figure 7A:
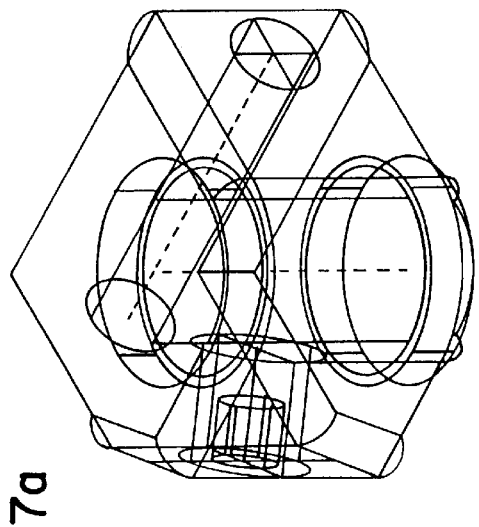

One advantageous feature is the positioning of the locking set screw 534 on an angled surface of the pivot block. FIG. 7a is a transparent view of this pivot block, absent the nut/head 544, showing the internal configuration. The arrangement of FIG. 7a is adapted for the left side of the jaw by the positioning of the set screw and its corresponding angled surface. A pivot block for the right side of the jaw as shown in FIG. 7c, in which it can be seen that the setscrew is moved to the other side of the hole employed for the thrust device. A transparent view together with the thrust device is illustrated in FIG. 7b for the left side.

Figure 7B:
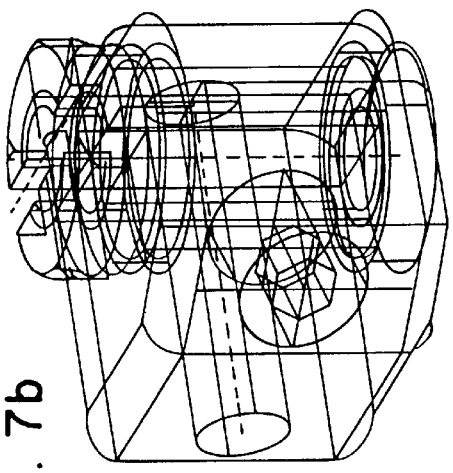

Thus, as shown in FIG. 7b, the device can be used for the left side of the patient's mouth, or even with the front lower teeth. With a suitable design of a pivot block, it can be used for other fight side or the left side, by simply turning it upside down for use in positioning in the opposite side of the jaw. For example, if one simply inverts the pivot block of 7a, the position of FIG. 7c can be obtained, so that a correct positioning of the same pivot block can be used for either side. In this case, the nut/head 544 and the thrust device should be removed the pivot block turned upside down, and the thrust device reinserted for use in the opposite side from its original adaptation. This permits access to the locking set screw for the thrust device from a forward facing position in the mouth no matter which side of the jaw is being operated on.

While the set screw 533 for the support bar is shown in one position, it is noted that it could be placed at any suitable location, as long as it is accessible.

Figure 8:
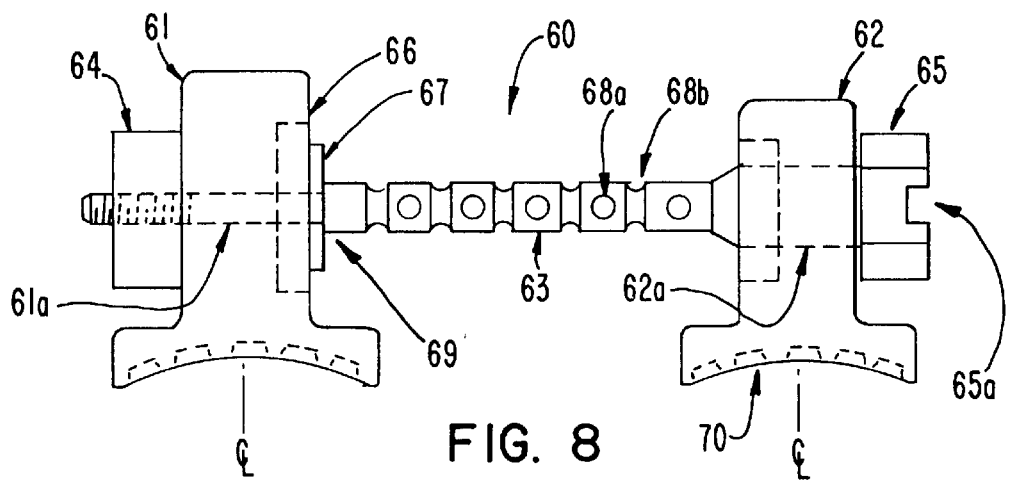
FIG. 8 is a plan view of a fifth embodiment of a distraction device according to the present invention.

FIG. 8 is a prospective view of a further distraction device 60 according to the present invention. With this embodiment, a posterior support 61 and anterior support 62 can preferably be mounted to the teeth, or possibly the bone, of the maxilla or mandible. The posterior and anterior support 61 and 62 have respective small and large holes 61a and 62a. A distraction member 63 is mounted in holes 61a and 62a for rotation therein. Reference numeral 70 indicates an adhesive bond location, at which location an adhesive bond can be employed to attach the supports 61 and 62 to the teeth of the patient on either side of the corticotomy site. Reference numeral 70a indicates sub surface details, i.e. small indentations, used to enhance the adhesive bond.

The distraction member 63 includes pull holes 68a and grooves 68b. The grooves 68b are provided between the pull holes 68a for guiding orthodontic wire. The orthodontic wire, shown for example in FIG. 16 with reference numeral 170, is attached to the distraction member 63 through the pull holes 68a. The grooves 68b are provided to receive the wire. A hex head 65 has a driver slot 65a at the anterior support for rotation of the distraction member 63 as a rotatable shaft.

The distraction member 63 has a shaft shoulder stop 69 adjacent to the posterior support 61. A metal clutch plate 67 is provided on the distraction member 63 and an elastomer clutch 66 is provided around the distraction member 63 and received in the posterior support 61. A fine nut 64 is threaded onto the end of the distraction member 63 to hold the distraction member 63 axially in place with respect to both the anterior support 61 and the posterior support 62. The elastomer clutch 66 and the metal clutch plate 67, together with the shaft shoulder stop, form a holding mechanism which can hold the rotatable shaft of the distraction member 63 in position without rotation unless a rotating force above a predetermined amount is applied to the rotatable shaft. The distracting member 63 together with the holding mechanism represent a distracting mechanism that is mounted on the intraoral support formed by the anterior and posterior supports 61 and 62. This mechanism is used to distract the orthodontic wire and thus the bone segment of the maxilla or mandible.

Figure 9:
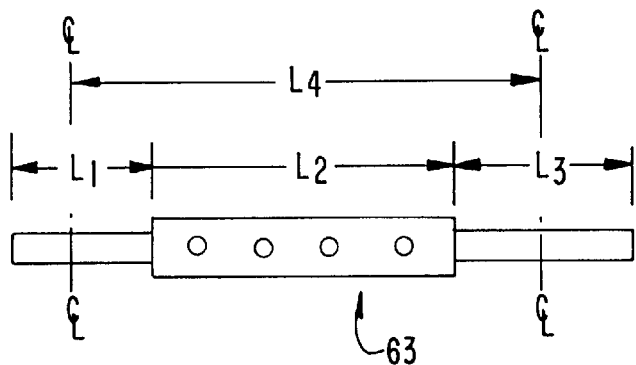
FIG. 9 is a schematic view of a rotatable shaft for use with the fifth embodiment.

FIG. 9 is a schematic view of the distraction member 63. This distraction member 63 has end portions L1 and L3 and a central portion L2 including rotatable shaft having the pull holes 68a. The distance L4 between the center lines of the anterior and posterior supports as shown by FIG. 9 is variable, for example between 3 and 50 mm, obviously depending on the circumstances; most situations will likely be in a range of 10 to 20 mm, and an example is 18.5 mm.

Figure 11:
FIG. 11 illustrates a miniature e-ring for use with the alternate arrangement of FIG. 10.
Figure 10:
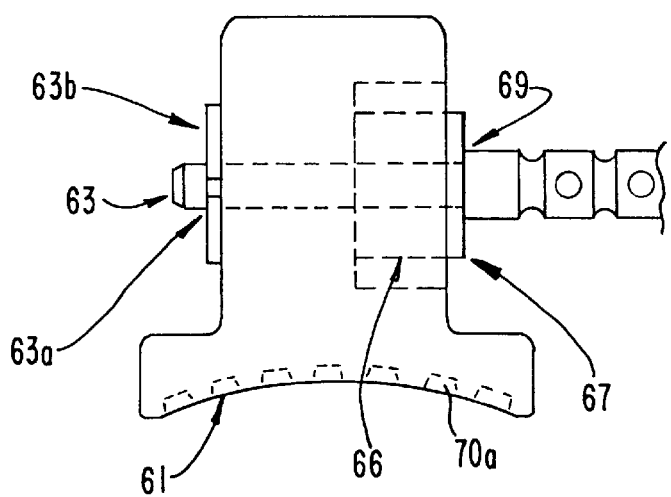
FIG. 10 is a detailed view of a posterior support for the distraction apparatus according the fifth embodiment, showing one alternative arrangement.

A variation of the embodiment of FIGS. 8 and 9 is illustrated by FIGS. 10 and 11. In this variation, instead of the fine nut 64, the distraction member 63 is provided with a shaft groove 63a and a miniature e-ring 63b. The miniature e-ring 63b holds the end of the shaft in place against the side surface of the posterior support 61.

In operation of both the embodiments of FIG. 8 and the variation of FIGS. 10 and 11, rotation of the distraction member 63 is made from the anterior end with a simple tool by engagement with the driver slot, for example. The elastomer clutch 66 and the metal clutch plate 67 provide a holding friction sufficient to hold the distraction member 63 in place during ordinary situations where no movement of the shaft and the bone segment is desired. However, this holding friction can be overcome by rotation of the distraction member 63 through the hex head 65, for example. A constant friction is provided by the clutch. Furthermore, this embodiment requires no compression or extension of the teeth via the supports in operation.

FIGS. 12–16 illustrate a variation of the fifth embodiment according to the present invention. In this variation, the distraction device 160, similar to the distraction device 60, includes a posterior support 161 and an anterior support 162 for connection to the teeth, or possibly bone, of a patient. The posterior and anterior supports 161 and 162 have respective holes receiving ends of a distraction member 163. The posterior support 161 is provided with a protruding detent 161a and an opposite space for receiving a wave washer 166 and a shaft shoulder stop 169 of the distraction member 163. The posterior support 161 further includes lateral support casting portions 170b and sub surface details 170a for interlocking with adhesive upon attachment to a tooth. The anterior support 162 includes a space for a hex head 165 similar to the hex head 65.

Figure 12:
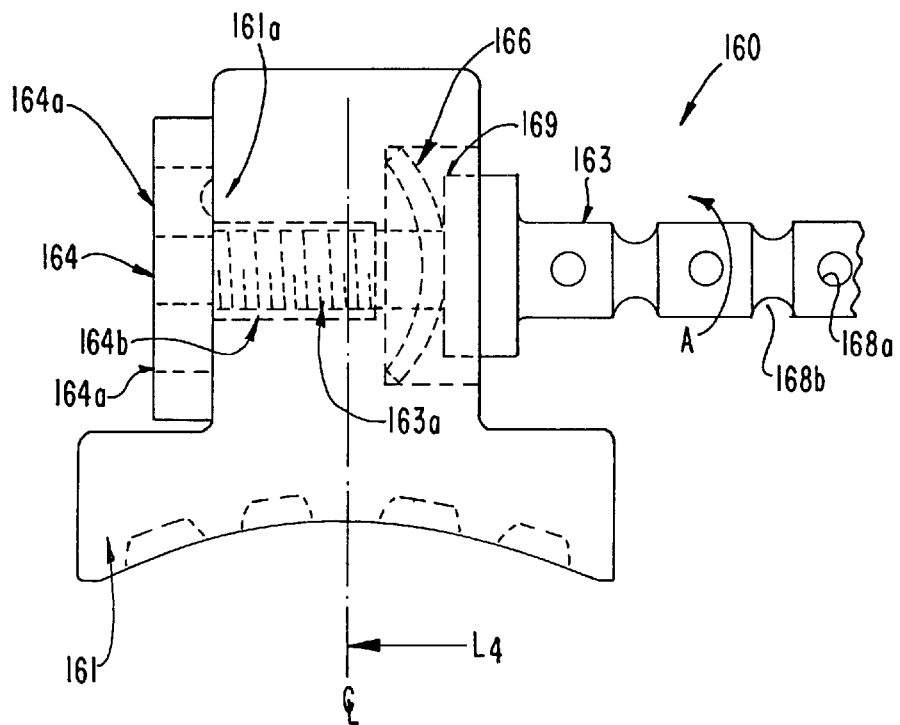
FIG. 12 is a detailed view of a further alternative arrangement in accordance with the fifth embodiment.
Figure 13:
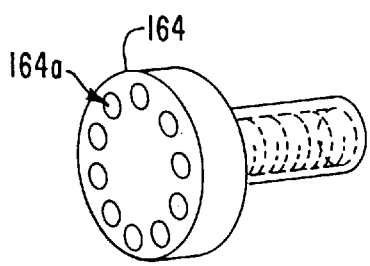
FIG. 13 is a perspective view of a threaded collar for use with the alternative of FIG. 12.
Figure 14:
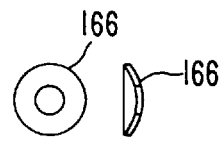
FIG. 14 illustrates a wave washer for use with the alternative of FIG. 12.

The distraction member 163, in addition to the hex head 165 at the anterior end, includes threads 163a at the posterior end. The threads 163a extend through the opening of the posterior support 161. The shaft shoulder stop 169 engages the wave washer 166 in the recess of the posterior support 161 as shown in FIG. 12. The threads 163a engage a threaded cylinder 164b of a threaded collar 164. The threaded collar 164 is inserted from the opposite side of the posterior support 161 and threaded onto the distraction member 163 as shown. The wave washer 166 is a light load wave washer providing an appropriate amount of biasing force to bias the distracting member 163 in the anterior direction. The threaded collar 164 is provided with the holes 164a, for example eight holes, as detent holes for receiving the detent 161a protruding from the posterior support.

With this arrangement, rotation of the distracting member 63 can be performed by applying a suitable force against the wave washer 166 at the hex head 165 to allow the posterior end of the distracting member 163 to push the thread collar 164 and the holes 164a off of the detent 161a so that rotation of the shaft can take place. The holes 164a are appropriately spaced around the threaded collar 164 so that movement from one hole to the next provides the appropriate amount of distraction for a single distraction step. The force of the wave washer 166 normally holds the threaded collar 164 in place with the detent 161a received in a respective hole 164a, thus maintaining the distracting member 163 in a non-rotatable position.

Note that threads 163a may require a light removable grade of thread locker adhesive or a patch, etc., in order to prevent counter rotation of threaded collar 164 with respect to the distraction member 163 when overcoming the protruding detents 161a during distraction.

Figure 16:
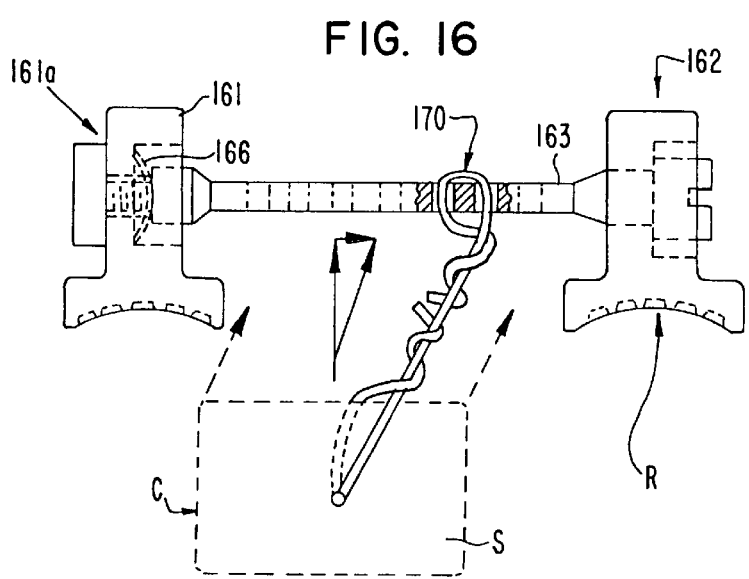
FIG. 16 illustrates the alternative of FIG. 12 and FIG. 15 in operation.

In this embodiment, pull holes 168a and grooves 168b can be provided, similar to the illustration of FIG. 8. In use, the distracting member 163 can be rotated to pull an orthodontic wire 170 as illustrated in FIG. 16. Here the site of the corticotomy is shown by C, and S indicates the segment for distraction. The direction of distraction can take place vertically, or substantially vertically (i.e. in a direction generally upward from the lines of the maxilla or mandible but with room for variation in the anterior or posterior direction as permitted by the adjacent teeth etc., with a resulting force direction as shown by the arrows in FIG. 16; the angle may also vary due to a need to adjust the force vector by relocation of the wire sometime during the distraction process in order to reposition the bone segment, and in this case there would be an angular movement deviating from the vertical; this angle could vary to 30 degrees, for example, from the vertical). The supports 161 and 162 are radiused, as shown by R, to match the crown of a tooth surface.

One alternative contemplated with respect to the present embodiments is to use attachments in accordance with U.S. Pat. No. 5,735,688 in place of direct bonding of the supports 161 and 162 to the teeth.

An advantage of the embodiments of FIGS. 8–16 is that FDA approved orthodontic stainless wire is all that engages the bone segment. Furthermore, the detent on the posterior support in FIG. 12 combined with a series of holes in the threaded collar (obviously the holes could be in the support and the detent on the threaded collar) provide fixed incremental stops to allow a rate of 1 mm movement of the wire, and thus of the bone segment.

Tension in the wire is maintained by the biasing force of the wave washer in axial compression holding the distraction member in place. The biasing force of the wave washer is chosen to provide a sufficient force to hold the detent engaged with the holes in the threaded collar under ordinary circumstances, while allowing the surgeon to displace the shaft against the force of the wave washer upon distraction of the bone segment. Tension on the wire is also caused due to a resistance force on the wire maintaining a low opposition force to the mechanism, the resistance force being caused by tissue/fibrous layer/cellular tension of the bone segment on the wire. In other words, the bone segment, without a cortex, causes a resistance force when the wire is stretched due to the connecting tissue, maintaining a tension on the wire, and thus the wire should never go slack.

The shaft of the distracting member is provided with a plurality of holes to allow repositioning of the wire during distraction in order to alter the vector force direction as necessary. Note for example FIG. 16 again. Adjustment, i.e. operation of the distracting member can be by a flat driver from the anterior end of the assembly. Otherwise, other types of drivers could be used.

The large radius on the base of the anterior and posterior supports matches the crown of a tooth, and the rough and sub surface details aid the adhesive bond.

Figure 17:
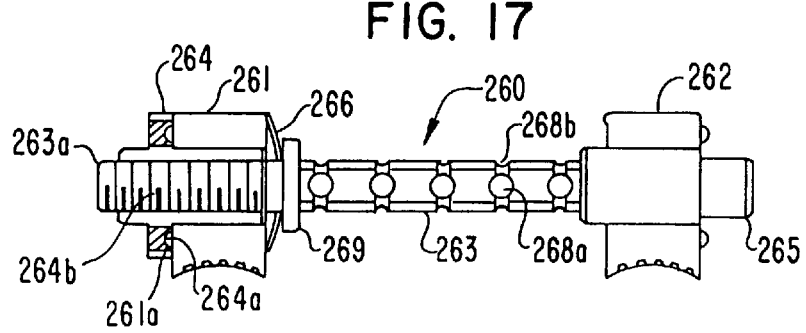
FIG. 17 illustrates a variation of the alternative of FIGS. 12 and 15.
Figure 15:
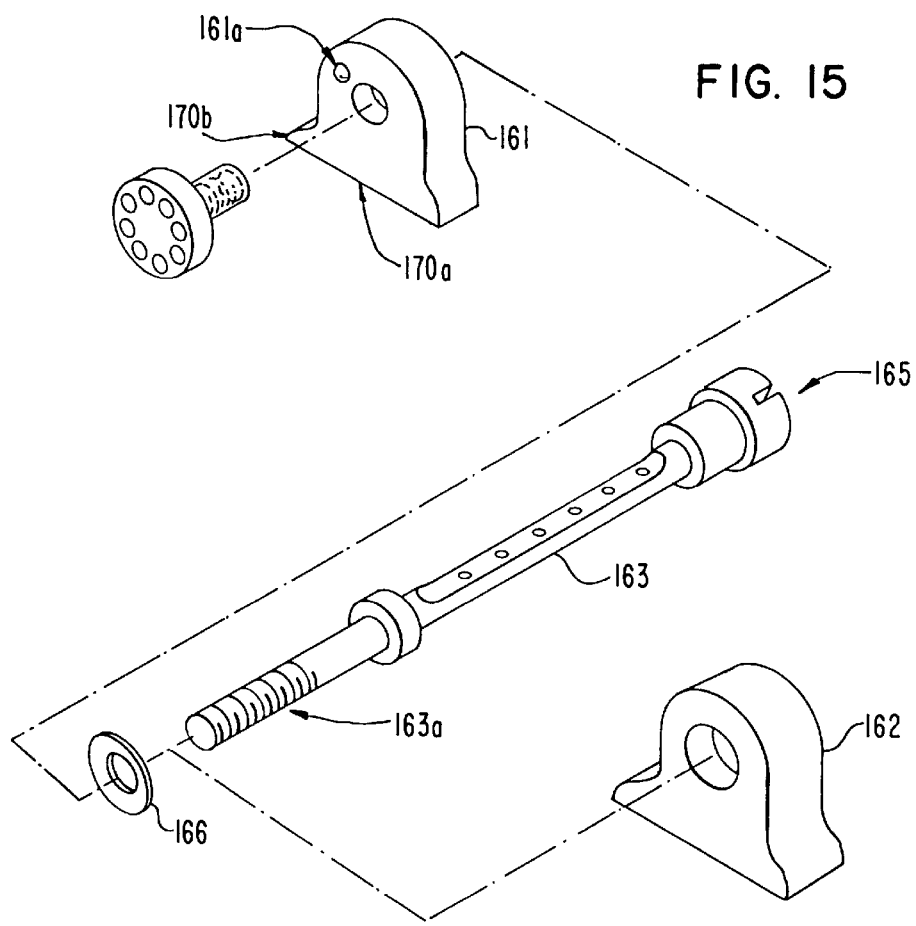
FIG. 15 is a perspective exploded view of a distraction device according to the present invention in accord with the alternative in FIG. 12.

Furthermore, various shaft lengths could be available to cover a range of segment sizes. A variation of the embodiment of FIGS. 12–16 is shown in FIG. 17. This distraction device 260 is similar in its basic components, including posterior and anterior supports 261 and 262, protruding detents 261a, distraction member 263 having threads 263a, threaded collar 264 having holes 264a and threaded cylinder 264b, wave washer 266, pull holes 268a, wire grooves 268b and shaft shoulder stop 269. The drive end 265 of the distraction member 263 is adapted here to receive a flat head screwdriver. Also, the threads 263a can extend all the way through the threaded collar 264. Further, the wave washer 266 is made larger and abuts the entire end surface of the posterior support 261, eliminating the need for a countersunk hole as in the earlier embodiment. Otherwise, the operation, advantages and effects are similar to the above discussed embodiments.

The invention as described in the embodiments as discussed above allows for gradual distraction of a bone section of the mandible or maxilla, on the order of 1 millimeter a day, in an exact amount and a precise direction. The direction of distraction can be precisely controlled, as can the amount, which could be set to an amount other than 1 mm, e.g. ½ mm. Thus, the bone ridge of the mandible or maxilla can be augmented using a relatively simple and straight forward mechanism, allowing substantially vertical distraction of the bone section in a simple manner. By this procedure providing for bone regeneration, and an increased bone mass, an implant can be inserted in the new new bone mass, or an impacted tooth could be brought in. Thus the present invention, in being able to regenerate bone tissue of the maxilla and mandible, enables a broader range of possibilities in facial and dental reconstruction. Of course, it should be recognized that various modifications and changes will occur to those of skill in the art. Such changes should be included within the scope of the present invention, as defined by the appended claims.

We claim:

1. An apparatus, comprising:

a support member adapted to be fixed with respect to one of the mandible and the maxilla;

a bone section engagement member adapted to engage a bone section of the one of the mandible and the maxilla; and a movement mechanism connecting said bone section engagement member with said support member for movement of said bone section engagement member relative to said support member;

wherein said support member comprises a bar having fixing members thereon for fixing said bar to the one of the mandible and the maxilla;

wherein said bone section engagement member comprises a shaft extending at an angle relative to said bar;

wherein said movement mechanism comprises a rotatable actuator and an engagement mechanism engaging said rotatable actuator with said shaft; and wherein said movement mechanism comprises a pivot block pivotally mounted on said bar and housing said rotatable actuator and said engagement mechanism.

2. An apparatus, comprising:

a support member adapted to be fixed with respect to one of the mandible and the maxilla;

a bone section engagement member adapted to engage a bone section of the one of the mandible and the maxilla; and a movement mechanism connecting said bone section engagement member with said support member for movement of said bone section engagement member relative to said support member;

wherein said bone section engagement member comprises a shaft extending at an angle relative to said support member;

wherein said movement mechanism comprises a rotatable actuator and an engagement mechanism engaging said rotatable actuator with said shaft;

wherein said rotatable actuator comprises a rotatable nut, and said engagement mechanism comprises internal threads of said nut and external threads on said shaft; and wherein a bearing supports said shaft at a position spaced from said rotatable nut.

3. An apparatus, comprising:

a support member adapted to be fixed with respect to one of the mandible and the maxilla;

a bone section engagement member adapted to engage a bone section of the one of the mandible and the maxilla; and a movement mechanism connecting said bone section engagement member with said support member for movement of said bone section engagement member relative to said support member;

wherein said bone section engagement member comprises a shaft extending at an angle relative to said support member, said shaft having external threads thereon; and wherein said movement mechanism comprises a rotatable actuator and an engagement mechanism engaging said rotatable actuator with said shaft; and wherein said rotatable actuator comprises a rotatable thrust device having a thrust collar, and said engagement mechanism comprises internal threads in said rotatable thrust device and said external threads on said shaft.

4. A distraction apparatus for subapical osteotomy and vertical segment distraction of a bone segment of the maxilla or mandible, comprising:

an intraoral support comprising a plurality of fixing members adapted to be fixed on teeth or bone of one of the mandible and maxilla on either side of the bone segment to be distracted;

an engagement member adapted to engage the bone segment to be distracted, said engagement member comprising a first portion engageable with the bone segment and a second portion spaced from the first portion; and a distracting mechanism mounted on said intraoral support between said fixing members, said distracting mechanism comprising a movable member engaged with said second portion of said engagement member such that when said movable member is moved, said engagement member is pulled in a direction substantially perpendicular to a line extending between said fixing members.

5. The distraction apparatus of claim 4, wherein said movable member of said distracting mechanism comprises a rotatable shaft rotatably mounted between said fixing members of said intraoral support.

6. The distraction apparatus of claim 5, wherein said distracting mechanism comprises a holding apparatus which can hold said rotatable shaft in position without rotation unless a rotating force above a predetermined amount is applied to said rotatable shaft.

7. The distraction mechanism of claim 6, wherein said holding mechanism comprises a metal clutch plate mounted on one of said fixing members and an elastomer clutch mounted on said rotatable shaft engaged with said metal clutch plate.

8. The distraction apparatus of claim 6, wherein said holding mechanism comprises a protrusion on one of said rotatable shaft and said intraoral support, a plurality of holes on the other of said rotatable shaft and said intraoral support, said protrusion being engaged with one of said holes, and a biasing member biasing said protrusion and the one of said holes into engagement with each other, wherein said rotatable shaft is axially movable to permit said protrusion to disengage from the one of said holes to allow said rotatable shaft to rotate.

9. The distraction apparatus of claim 5, wherein said fixing members comprise a posterior support and an anterior support each having respective holes there through receiving said rotatable shaft therein.

10. The distraction apparatus of claim 9, wherein said rotatable shaft comprises a driving head adjacent to said anterior support and said distracting mechanism comprises a holding mechanism which can hold said rotatable shaft in position without rotation unless a rotating force above a predetermined amount is applied to said rotatable shaft adjacent to said posterior support.

11. The distraction apparatus of claim 4, wherein said rotatable shaft is mounted to said fixing members by respective bearings for rotation relative thereto.

12. The distraction apparatus of claim 4, wherein said rotatable shaft comprises a plurality of pull holes therein and said engagement member comprises wire, said wire including said first portion and said second portion, with said second portion being engaged through one of said pull holes so that the bone segment can be distracted by rotation of said rotatable shaft.

13. The distraction apparatus of claim 12, wherein said rotatable shaft further comprises wire grooves between said pull holes.

14. The distraction apparatus of claim 4, wherein:

said intraoral support comprises a bar having said fixing members thereon for fixing said bar to the one of the mandible and the maxilla;

wherein said engagement member comprises a shaft extending at an angle relative to said bar;

wherein said distracting mechanism comprises a rotatable actuator and an engagement mechanism engaging said rotatable actuator with said shaft; and wherein said distracting mechanism comprises a pivot block pivotally mounted on said bar and housing said rotatable actuator and said engagement mechanism.

15. The distraction apparatus of claim 4, comprising:

wherein said bone segment engagement member comprises a shaft extending at an angle relative to said intraoral support;

wherein said distracting mechanism comprises a rotatable actuator and an engagement mechanism engaging said rotatable actuator with said shaft;

wherein said rotatable actuator comprises a rotatable nut, and said engagement mechanism comprises internal threads of said nut and external threads of said shaft; and wherein an unthreaded bearing supports said shaft at a position spaced from said rotatable nut.

16. The distraction apparatus of claim 4, comprising:

wherein said engagement member comprises a shaft extending at an angle relative to said intraoral support; and wherein said distracting mechanism comprises a rotatable actuator and an engagement mechanism engaging said rotatable actuator with said shaft; and wherein said rotatable actuator comprises a rotatable thrust device having a thrust collar, and said engagement mechanism comprises internal threads in said rotatable thrust device and external threads on said shaft.

17. The distraction apparatus of claim 4, wherein said fixing members comprise anterior and posterior supports having tooth engagement surfaces having a shape adapted to match the surface of teeth to which said supports are to be attached.

18. The distraction apparatus of claim 4, wherein said fixing members comprise anterior and posterior supports, tooth engagement members and attachments for detachably connecting said anterior and posterior supports with said tooth engagement members.

19. A distraction apparatus for subapical osteotomy and vertical segment distraction of a bone segment of the maxilla or mandible, comprising:

an intraoral support comprising a plurality of tooth fixing members adapted to be fixed on teeth of the mandible and maxilla on either side of the bone segment to be distracted;

an engagement member adapted to engage the bone segment to be distracted, said engagement member comprising a first portion engageable with the bone segment and a second portion spaced from the first portion; and a distracting mechanism mounted on said intraoral support between said fixing members, said distracting mechanism comprising a movable member engaged with said second portion of said engagement member such that when said movable member is moved, said engagement member is pulled in a direction toward said distracting mechanism.

* * * * *